(12) United States Patent
De Pater et al.

(10) Patent No.: US 8,461,327 B2
(45) Date of Patent: Jun. 11, 2013

(54) DIAMINE SALTS OF CARBOXYLIC ACIDS

(75) Inventors: Robertus Mattheus De Pater, Delft (NL); Adrianus Antonius Cornelius Van Wijk, Delft (NL); Piotr Wnukowski, Delft (NL)

(73) Assignee: DSM Sinochem Pharmaceuticals Netherlands B.V., Delft (NL)

( * ) Notice: Subject to any disclaimer, the term of this patent is extended or adjusted under 35 U.S.C. 154(b) by 172 days.

(21) Appl. No.: 12/936,361

(22) PCT Filed: Mar. 31, 2009

(86) PCT No.: PCT/EP2009/053790
§ 371 (c)(1),
(2), (4) Date: Oct. 4, 2010

(87) PCT Pub. No.: WO2009/121869
PCT Pub. Date: Oct. 8, 2009

(65) Prior Publication Data
US 2011/0028712 A1 Feb. 3, 2011

(30) Foreign Application Priority Data

Apr. 2, 2008 (EP) .................................. 08103322

(51) Int. Cl.
*C07D 487/08* (2006.01)
*C07D 307/00* (2006.01)
*C07C 67/02* (2006.01)

(52) U.S. Cl.
USPC ........................... 540/349; 549/469; 560/258

(58) Field of Classification Search
None
See application file for complete search history.

(56) References Cited

U.S. PATENT DOCUMENTS

| 4,713,201 | A | * | 12/1987 | Pilz et al. | ...................... 562/480 |
| 5,786,351 | A | * | 7/1998 | Callewaert | ................ 514/210.09 |
| 2003/0207413 | A1 | | 11/2003 | Jekkel et al. | |

FOREIGN PATENT DOCUMENTS

| EP | 0 209 733 | 1/1987 |
| WO | WO 96/20199 | 7/1996 |

OTHER PUBLICATIONS

International Search Report for PCT/EP2009/053790, mailed May 29, 2009.

* cited by examiner

*Primary Examiner* — Sudhakar Katakam
*Assistant Examiner* — Clinton Brooks
(74) *Attorney, Agent, or Firm* — Nixon & Vanderhye P.C.

(57) ABSTRACT

The present invention relates to a salt of a carboxylic acid with a diamine such as 2,2'-(ethylenedioxy)diethyl amine, 3,3'-(ethylenedioxy)dipropyl amine and 2,2'-oxybis(ethylamine) and a method of preparing such salts. Preferably the carboxylic acid is a fermentation product such as clavulanic acid, mycophenolic acid or pravastatin.

4 Claims, No Drawings

DIAMINE SALTS OF CARBOXYLIC ACIDS

This application is the U.S. national phase of International Application No. PCT/EP2009/053790 filed 31 Mar. 2009, which designated the U.S. and claims priority to EP Application No. 08103322.7 filed 2 Apr. 2008, the entire contents of each of which are hereby incorporated by reference.

FIELD OF THE INVENTION

The present invention relates to diamine salts of carboxylic acids and a method for the recovery of carboxylic acids obtained by fermentation through formation of said diamine salts.

BACKGROUND OF THE INVENTION

Isolation and purification of carboxylic acids are important industrial processes that can be quite difficult to accomplish when such carboxylic acids are prepared in complex mixtures such as, for instance, fermentation broths. Well-known examples of such fermentatively prepared carboxylic acids are the classes of β-lactams such as for example clavulanic acid, penicillin G and penicillin V, statins such as for example compactin, lovastatin, mevastatin, pravastatin and simvastatin, (poly-)unsaturated fatty acids such as for example arachidonic acid, docosahexaenoic acid, eicosapentaenoic acid, linoleic acid, linolenic acid and retinoic acid and other molecules of industrial relevance such as for example biotin, cholic acid, enteromycin, fusidic acid, helvolic acid, jasmonic acid, lactobacillic acid, laidlomycin, mycophenolic acid, pimaric acid, prostaglandin, rifamycin B, shikimic acid and the like.

The processes for the isolation and purification of these carboxylic acids known from patent and technical literature include different combinations of extraction, chromatography and crystallization methods. Some of them additionally include isolation and purification via different salts.

For example, in U.S. Pat. Nos. 4,342,767 and 4,319,039, the ammonium salt of lovastatin is isolated from an organic phase which has been extracted from the fermentation medium. Also disclosed are salts of lovastatin with ethylene diamine, tetramethylammonia, N-methylglucamine, L-lysine, L-arginine and L-ornithine. In EP 65,835 various salts of tetrahydro-M-4 or tetrahydro-isoM-4 (wherein M-4 denotes a specific HMG-CoA reductase inhibitor) are suggested, such as salts with octyl amine, 2-ethylhexyl amine, benzyl amine, α-methyl-benzyl amine, phenethyl amine, dibenzyl amine, N-methylbenzyl amine, N,N-dimethylbenzyl amine, N,N-diethylbenzyl amine, N-ethyl-N-methylbenzyl amine, tribenzyl amine, cyclopentyl amine, cyclohexyl amine cycloheptyl amine, N-methylcyclopentyl amine, N-ethylcyclohexyl amine, N-ethylcycloheptyl amine, dicyclohexyl amine, N,N-dimethylcyclopentyl amine, N,N-dimethylcyclohexyl amine, N,N-diethylcycloheptyl amine, pyrrolidine, N-methylpyrrolidine, piperidine, N-methylpiperidine and morpholine. GB 2073199 also discloses the preparation of different salts of HMG-CoA reductase inhibitors from the already isolated substance in the lactone form. U.S. Pat. Nos. 5,763,653 and 5,763,646 disclose the preparation of the cyclopropyl amine and n-butyl amine salts of lovastatin. U.S. Pat. No. 6,838,566 describes the formation of salts of atorvastatin, lovastatin, mevastatin, pravastatin and simvastatin with specific amines, namely adamantyl amine, 2-amino-3,3-dimethylbutane, 3-(2-aminoethylamino)-propyl amine, tert-amyl amine, n-butyl amine, sec-butyl amine, tert-butyl amine, cyclobutyl amine, cycloheptyl amine, cyclohexyl amine, cyclopentyl amine, dibutyl amine, dicyclohexyl amine, N,N-diethylcyclohexyl amine, N,N'-diethylene diamine, N,N'-diisopropylethylene diamine, N,N-dimethylcyclohexyl amine, (±)-1,2-dimethylpropyl amine, 1,2-dipiperidinethane, dipiperidinemethane, N-isopropylcyclohexyl amine, N-methylcyclohexyl amine, N-methylethylene diamine, N-methyl-1,3-propane diamine, neopentyl amine, norboryl amine, N,N,N',N'-tetramethyl-1,4-diaminobutane, N,N,N',N'-tetramethyl-1,2-diaminoethane and N,N,N',N'-tetramethyl-1,6-diaminohexane.

Similar approaches are also known for other fermentatively prepared carboxylic acids, such as the β-lecterns. In case of clavulanic acid, the product may be extracted in an organic phase and crystallized as a salt of clavulanic acid with an organic amine, and isolating such an amine salt. In such a process the amine salt is formed as an intermediate in the process of converting crude clavulanic acid into a pharmaceutically acceptable salt. Such a process is described in for example EP 26044, in which a solution of impure clavulanic acid in an organic solvent is contacted with tert-butyl amine to form the tert-butyl amine salt of clavulanic acid, which is then isolated. Other similar processes are known which use other organic amines, such as tert-octyl amine (EP 594099) diethyl amine, tri-(lower alkyl) amines, dimethylaniline and N,N'-diisopropyl-ethylene diamine. WO 93/25557 discloses a very extensive list of amines which can be used in this way. WO 94/22873 discloses use of various tertiary diamines such as N,N,N',N'-tetramethyl-1,2-diaminoethane, N,N,N',N'-tetramethyl-1,6-diaminohexane, 1,2-dipiperidinoethane and dipiperidinomethane. WO 96/20199 discloses the use of bis(2-dimethylaminoethyl)ether. GB 2298201 discloses the use of various benzhydryl amines. WO 96/33197 discloses the use of further amines including symmetrical N,N'-alkylethylene diamines, such as N,N'-diisopropyl-ethylene diamine, N,N'-diethylene diamine, N,N'-dibenzylethylene diamine and N,N,N',N'-tetramethylene diamine. WO 98/21212 discloses clavulanic acid salts with the amines N,N,N',N'-tetramethylethylene diamine, 1,3-bis(di-methylamino)-2-propanol, benzhydryl amine and bis(2-(dimethylamino)ethyl)ether. Finally, WO 98/23622 discloses diisopropylethylene diamine clavulanic acid salt.

Also for mycophenolic acid, several amine salts have been described. In WO 04/20426 the dibenzyl amine, ammonium and dicyclohexyl amine salts have been described and in Aust. J. Chem. (1978), 31, 353-64, the triethyl amine salt is described.

Indeed many amine salts of fermentatively prepared carboxylic acids have been described. Nevertheless, in industry there exists a constant need for rationalization of the production and shortening of the production processes as well as for the use of inexpensive starting materials. Therefore, there is a constant need for alternative salts of carboxylic acids, preferably with properties similar or improved compared to those described in the art.

DETAILED DESCRIPTION OF THE INVENTION

In a first aspect, the present invention relates to a salt of a carboxylic acid with a diamine of general structure [1]

$$H_2N-(CH_2)_a-O-(CH_2)_b-(O)_c(CH_2)_d-NH_2 \qquad [1]$$

wherein a is 1, 2, 3 or 4, b is 0, 1, 2, 3 or 4, c is 0 or 1, d is 1, 2, 3 or 4 and c is 0 when b is 0.

Although many amine salts of carboxylic acids have been described, as outlined above, only relatively few disclosures are known where unsubstituted diamine salts are mentioned. Nevertheless these diamine salts, such as the ones of the present invention, can readily form crystals. In addition, some have the advantage that they form crystals wherein one molecule of diamine is combined with two molecules of carboxylic acid. The result of this phenomenon is that a relatively low amount of diamine is required which is favorable from an environmental, an economic and a process technical point of view.

In a first embodiment, c in [1] is 0. A preferred example is 2,2'-oxybis(ethylamine).

In a second embodiment, c in [1] is 1 and a is equal to d. Preferred examples are 2,2'-(ethylenedioxy)diethyl amine (ethyldiethanolamine, EDEA) and 3,3'-(ethylenedioxy) dipropyl amine.

In a third embodiment, the carboxylic acid of the present invention preferably is a mono-carboxylic acid. A mono-carboxylic acid is a compound with only one group $CO_2H$ covalently attached to the compound. Although the present invention is suitable for all carboxylic acids, an additional advantage associated with mono-carboxylic acids is that, on a molar basis, per two molecules mono-carboxylic acid only one molecule of diamine is needed which is beneficial from an economic as well as an environmental point of view.

In a fourth embodiment, the carboxylic acid of the present invention is a fermentation product. Where the salts of the present invention are suitable for the isolation and purification of carboxylic acids in general, fermentatively derived carboxylic acids are notoriously difficult to isolate and purify and the salts of the present invention are particularly suitable for this purpose. Thus the salts of the present invention are salts of carboxylic acids that are fermentation products such as β-lactams, statins, (poly-)unsaturated fatty acids and other molecules of industrial relevance. Preferred examples of such carboxylic acids are arachidonic acid, biotin, cholic acid, clavulanic acid, compactin, docosahexaenoic acid, eicosapentaenoic acid, enteromycin, fusidic acid, helvolic acid, jasmonic acid, lactobacillic acid, laidlomycin, linoleic acid, linolenic acid, lovastatin, mevastatin, mycophenolic acid, penicillin G, penicillin V, pimaric acid, pravastatin, prostaglandin, retinoic acid, rifamycin B, shikimic acid and simvastatin. In the context of the present invention, the term 'statin' or more in particular the statins compactin, lovastatin, mevastatin, pravastatin and simvastatin refer to compounds that can exist in a closed-ring lactone form or in an open hydroxy carboxylic acid form. A salt of such a statin is a salt of the open hydroxy carboxylic acid.

In a second aspect, the present invention provides a method for the preparation of the carboxylic acid diamine salts of the first aspect comprising treatment of a carboxylic acid with a diamine of general structure [1]

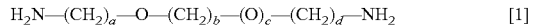

$$H_2N\text{---}(CH_2)_a\text{---}O\text{---}(CH_2)_b\text{---}(O)_c\text{---}(CH_2)_d\text{---}NH_2 \qquad [1]$$

wherein a is 1, 2, 3 or 4, b is 0, 1, 2, 3 or 4, c is 0 or 1, d is 1, 2, 3 or 4 and c is 0 when b is 0.

In one embodiment, the carboxylic acid can be any commercially available carboxylic acid with a purity ranging from 50 to 100%. Preferably the carboxylic acid is dissolved in an organic solvent. Preferred solvents are esters such as methyl acetate, ethyl acetate, iso-propyl acetate and the like. Other preferred solvents are ketones such as methyl iso-butyl ketone and the like. Other suitable solvents are water-immiscible solvents examples of which are chloroform, dichloromethane, toluene, xylene and derivatives thereof. Alternatively, the starting material can be a salt of the carboxylic acid. Examples of such salts are amine, magnesium, potassium, sodium and similar salts. In this case the carboxylic acid is obtained by dissolving the carboxylic acid salt in water and extracting the aqueous phase thus obtained with a water-immiscible solvent as described above at low pH. Preferably the concentration of carboxylic acid in organic solvent is from 5 to 500 g/L, more preferably from 10 to 250 g/L, most preferably from 20 to 100 g/L, depending on the solubility of the carboxylic acid and solvent in question. In a preferred embodiment the solution of carboxylic acid in organic solvent is dried, either by addition and subsequent removal of drying materials such as molecular sieves or any of the drying salts known to the skilled person such as magnesium sulfate, sodium sulfate and calcium chloride and the like. Another possibility is azeotropic removal of traces water by distillation of part of the solvent. Removal of water increases yield and/or purity of the final product. Azeotropic distillation has the additional advantage of concentration of the solution which can result in further yield improvement. Also removal by non-azeotropic distillation is possible.

In a second embodiment, the present invention relates to a new process for isolation and/or purification of fermentatively prepared carboxylic acids via salts thereof with diamines of general structure [1]. The invention enables to obtain the pure carboxylic acid diamine salts from the fermentation broth. The salts thus formed may be used as the starting substances or intermediates for the preparation of semi synthetic derivatives and analogs thereof, or by employing simple techniques known from the literature, if required, to be converted into the pharmaceutically acceptable salts and lactones, respectively. Preferably, the fermentatively derived carboxylic acid is extracted from the aqueous fermentation broth into a water-immiscible solvent at low pH. Any cells or cell materials can be removed prior to the extraction step by standard procedures such as filtration or centrifugation that are known to the skilled person. Alternatively the extraction is carried out on the fermentation broth as is (i.e. whole-broth extraction).

In a third embodiment, the amount of diamine relative to the amount of carboxylic acid is expressed in molar ratio. Preferably the molar ratio of carboxylic acid to diamine is ranging from 3:1 to 1:20, more preferably from 2:1 to 1:5, most preferably from 2:1 to 1:1 or from 2:1 to 20:11. The diamine of general structure [1] can be added directly to the solution of carboxylic acid or dissolved in an organic solvent. The latter facilitates controlled addition. The organic solvent can be the same as the one used to dissolve the carboxylic acid; however this is by no means mandatory for a successful outcome of the method of the second aspect but can serve to facilitate solvent recovery. Alternatively, the solution of carboxylic acid can be added to the diamine of general structure [1] or to a solution thereof. Formation of crystals of carboxylic acid diamine salts of the first aspect either occurs at room temperature but can also be facilitated by lowering the temperature of the mixture. Preferably the temperature is lowered to a temperature ranging between −80° C. and 15° C., more preferably between −50° C. and 10° C., most preferably between −20° C. and 0° C.

In a third aspect of the present invention, the carboxylic acid diamine salts of the first aspect is suitably used as starting material or intermediate in a process for preparing a medicament. This can be by converting the carboxylic acid diamine salt of the invention into the active pharmaceutical ingredient, which may be a different salt or a free carboxylic acid. Specific examples of such pharmaceutical active ingredients are the sodium salts of clavulanic acid, mycophenolic acid and pravastatin, but also the further chemical conversion into an active pharmaceutical ingredient such as mycophenolate mofetil or simvastatin. The active pharmaceutical ingredient is then converted into a medicament according to procedures known to the skilled person.

EXAMPLES

HPLC Analysis

HPLC analysis was based on reversed phase liquid chromatography followed by UV-detection at 238 nm.

Apparatus: Dionex HPLC-UV system comprising of a P680 pump, a TCC-100 column compartment with thermostat, a WPS-3000 auto sampler and a UVD34OU PDA detector.

Conditions:

| | |
|---|---|
| Column: | Waters Sunfire C18, 150 × 4.6 mm, 3.5 µm |
| Column temp: | 40° C. |
| Flow rate: | 1.2 ml/min |
| UV-detection | 238 nm |
| Injection volume: | 10 µl |
| Sample tray temp: | 5° C. |
| Mobile phase A: | 0.1% formic acid in methanol-Milli-Q purified water (6/4) v/v |
| Mobile phase B: | 0.04% formic acid in acetonitrile |
| Gradient: | T = 0 min.    0% B |
| | T = 5 min.    0% B |
| | T = 15 min.  60% B |
| | T = 16 min.  60% B |
| | T = 17 min.   0% B |
| | T = 20 min.   0% B |

Materials: Water: Milli-Q purified water or HPLC grade; acetonitrile, gradient grade, Merck art. Nr. 1.00030; methanol, gradient grade, Merck art. Nr. 1.06007; formic acid, Gr for analysis, Merck art. Nr.1.00264.

Procedures: Mobile phases:

Mobile phase A: Mix 600 ml methanol, 400 ml MilliQ-purified water and 1 ml formic acid.

Mobile phase B: Add 0.4 ml formic acid to 1 liter acetonitrile.

Masses are determined using a Waters HPLC/MS-UV under the same chromatographic conditions as described above (Waters Acquity Ultra Performance LC with PDA detector coupled to a Quattro Micro mass spectrometer).

Example 1

Preparation of Pravastatin 2,2'-(ethylenedioxy)diethyl Amine Salt from a Solution of Pravastatin in Ethyl Acetate Commercially available pravastatin sodium salt (10 g) was dissolved in water (250 mL). Ethyl acetate (200 mL) was added and the pH of the solution was adjusted to 4. A precipitate was formed, which slowly dissolved in the organic phase. The organic phase was separated from the aqueous phase and dried with $MgSO_4$ (10 g). The solids were removed by filtration and washed with ethyl acetate (50 mL) resulting in a pravastatin solution of ~40 g/L. 2,2'-(Ethylenedioxy)diethyl amine (EDEA, $H_2N$—$(CH_2)_2$—O—$(CH_2)_2$—O—$(CH_2)_2$—$NH_2$, 0.5 equivalents) was dissolved in ethanol (3 mL) and slowly (15-30 minutes) pravastatin solution (10 mL in ethyl acetate) obtained above was added. After complete addition a clear, green solution was obtained. After stirring the solution for 45 minutes at room temperature, a white solid precipitate was formed. After stirring for 1.5 hours the precipitate was collected by filtration, washed with 25% ethanol/ethyl acetate and dried in vacuo to give the bis-pravastatin salt of 2,2'-(ethylenedioxy)diethyl amine with the following characteristics:

Melting point 163-164° C.;

$UV_{max}$ 238.1 nm;

HPLC retention time 4.80 min.;

With HPLC/MS-UV the mass of the main component is determined: next to the fragmentation ions, the clusters of $[M+H]^+=425$, $[M+Na]^+=447$ and $[M+K]^+=463$ can be identified in this spectrum. So, the molecular mass of this compound is 424 Dalton corresponding to pravastatin acid. With the average molecular weights of pravastatin (424.536 Da) and EDEA (148.206 Da) the content of pravastatin-EDEA salt in the sample is calculated for a pravastatin/EDEA ratio of 1:1 (111.6%) and 1:2 (97.2%). Hence the pravastatin/EDEA ratio is 1:2 (also confirmed from $^1H$ NMR, see below);

$^1H$ NMR (600 MHz, $CD_3OD$): δ 0.90 (d, 6H, $CH_3$-21 and $CH_3$-8), 1.11 (d, 3H, $CH_3$-19'), 1.23 (m, 1H, H-12'), 1.39 (m, 2H, H-2' and H-12"), 1.44 (m, 1H, H-11'), 1.52-1.66 (m, 5H, H-11", 2×H-14, and 2×H-20), 1.69 (m, 1H, H-9), 2.26 (dd, 1H, J=15.2 Hz and J=8.2 Hz, H-16'), 2.33-2.42 (m, 4H, H-8, H-10, H-16" and H-19), 2.48 (m, 1H, H-2"), 3.09 (t, 4H, $ND_2CH_2CH_2O$—), 3.68 (t, 4H, $ND_2CH_2CH_2O$—), 3.69 (m, 1H, H-13), 3.70 (s, 4H, —$OCH_2CH_2O$—), 4.09 (m, 1H, H-15), 4.30 (m, 1H, H-3), 5.36 (bs, 1H, H-1), 5.51 (bs, 1H, H-4), 5.88 (dd, J=9.7 Hz and J=5.9 Hz, H-7), 5.98 (bd, 1H, J=10 Hz, H-6).

Example 2

Preparation of Pravastatin 2,2'-(ethylenedioxy)diethyl Amine Salt from a Solution of Pravastatin in Methylisobutyl Ketone Example 1 was repeated, however with methylisobutyl ketone instead of ethyl acetate; the results were similar as in Example 1.

Example 3

Preparation of Pravastatin 2,2'-oxybis(ethylamine) Salt from a Solution of Pravastatin in Methylisobutyl Ketone Example 2 was repeated, however with 2,2'-oxybis(ethylamine) ($H_2N$—$(CH_2)_2$—O—$(CH_2)_2$—$NH_2$) instead of EDEA. Addition of the pravastatin solution in methylisobutyl ketone to a solution of 2,2'-oxybis(ethylamine) resulted in a turbid, pink suspension. Methanol (0.3 mL) was added and the mixture was gently heated to dissolve the precipitate. Subsequently, the mixture was stored at −18° C. to start crystallization and crystals were isolated after a few days. The product displayed similar $^1H$ NMR characteristics as described in Example 1.

Example 4

Preparation of Mycophenolic Acid 2,2'-(ethylenedioxy)diethyl Amine Salt from a Solution of Mycophenolic Acid in Ethyl Acetate Commercially available mycophenolic acid (0.94 g, 2.93 mmol) was dissolved in ethyl acetate (25 mL) by heating the mixture to 60° C. 2,2'-(Ethylenedioxy)diethyl amine (EDEA, $H_2N$—$(CH_2)_2$—O—$(CH_2)_2$—O—$(CH_2)_2$—$NH_2$, 1.47 mmol, 0.5 equivalents) was dissolved in ethyl acetate and slowly (15-30 minutes) added to the solution of mycophenolic acid. During addition, a white precipitate was formed. After complete addition the suspension was allowed to slowly cool down to room temperature and further cooled to 4° C. The white solid precipitate was collected by filtration, washed with ethyl acetate and dried in vacuo to yield 0.68 g (1.45 mmol, 98.8% yield based on EDEA) of the mono-mycophenolate salt of 2,2'-(ethylenedioxy)diethyl amine. $^1$H-NMR (600 MHz) CD$_3$OD: δ 1.81 (s, 3H, CH$_3$—C=), 2.14 (s, 3H, CH$_3$—Ar), 2.23-2.35 (m, 4H, DOOC—CH$_2$—CH$_2$—C=), 2.95 (t, 4H, D$_2$N—CH$_2$—CH$_2$—), 3.38 (d, 2H, J$_3$=6.8 Hz, Ar—CH$_2$—CH=), 3.62 (t, 4H, D$_2$N—CH$_2$—CH$_2$—O—), 3.67 (s, 4H, —O—CH$_2$—CH$_2$—O—), 3.76 (s, 3H, O—CH$_3$), 6.23 (s, 2H, —CH$_2$—CO), 5.24 (t, 1H, Ar—CH$_2$—CH=).

Example 5

Preparation of Clavulanic Acid 2,2'-(ethylenedioxy)diethyl Amine Salt from a Solution of Clavulanic Acid in Ethyl Acetate The potassium salt of clavulanic acid (1 g; 60% potassium clavulanate; composition potassium clavulanate/Avicell=1.5/1) was dissolved in water (25 mL). Ethyl acetate (100 mL) was added and the pH was adjusted to 1.8 with 6N sulfuric acid. The phases were separated and the organic phase was concentrated to 10 mL under vacuum. The solution was diluted with ethanol (2 mL). At 20° C. a mixture of 2,2'-(ethylenedioxy)diethyl amine (EDEA, H$_2$N—(CH$_2$)$_2$—O—(CH$_2$)$_2$—O—(CH$_2$)$_2$—NH$_2$, 150 µL) and ethanol (150 µl) was added drop-wise under stirring. Oil precipitated from the solution. After cooling the supernatant was decanted and the oil was triturated with diethyl ether, giving the title product as a yellowish to orange solid.

Example 6

Preparation of Clavulanic Acid 2,2'-(ethylenedioxy)diethyl Amine Salt from a Solution of Clavulanic Acid in Ethyl Acetate The potassium salt of clavulanic acid (1 g; 60% potassium clavulanate; composition potassium clavulanate/Avicell=1.5/1) was dissolved in water (25 mL). Ethyl acetate (100 mL) was added and the pH was adjusted to 1.8 with 6N sulfuric acid. The phases were separated and the organic phase was concentrated to 10 mL under vacuum. Under stirring this solution was added drop-wise to a mixture of ethanol (3 mL) and 2,2'-(ethylenedioxy)diethyl amine (EDEA, H$_2$N—(CH$_2$)$_2$—O—(CH$_2$)$_2$—O—(CH$_2$)$_2$—NH$_2$, 150 µL). Oil precipitated from the solution. The supernatant was decanted and the oil was triturated with diethyl ether, giving the title product as a yellowish to orange solid.

Example 7

Preparation of Pravastatin 2,2'-(ethylenedioxy)diethyl Amine Salt from a Fermentation Broth Using Multi Stage Cross-current Back-extraction from Ethyl Acetate at pH 5.9

Starting material for this experiment was broth filtrate, obtained after ultra-filtration of broth obtained by fermentation of *Penicillium chrysogenum* transformant T1.48 as described in Example 4 of WO 2007/147827 using a 50 nm poly-sulfone membrane. The filtrate (5.25 liter, containing 1.2 g/l pravastatin and 0.37 g/l compactin) was extracted twice with ethyl acetate (2×2.5 liter) at pH 4. For a clear phase separation, the organic phases were filtered through a Seitz Z-2000 filter plate. The extraction yields were 90.6% and 8.3% respectively, so the overall extraction yield was 98.9%.

The organic phases were combined and washed with water (2.5 liter), giving ethyl acetate extract (4.65 liter, yield over the wash step 97%) which was concentrated to 250 ml under vacuum at T<40° C., giving a clear solution containing ~25 g/l pravastatin. This solution was extracted three times with water (3×250 ml) at pH 5.9. The pH was adjusted with 4N sodium hydroxide. Ethyl acetate was added to 440 ml of the combined first two aqueous phases and pravastatin was extracted to the organic phase at pH=4 which was concentrated to a final volume of 120 ml in which the concentration of pravastatin was determined with HPLC to be 34 g/l. This solution was treated with carbon using a cartridge filled with a Cuno R55 carbon plate containing 1.8 g active carbon. The pravastatin-containing fractions were pooled, treated with Norit SX-ultra carbon (2 g) and concentrated to a volume in which the concentration of pravastatin was determined with HPLC to be 40 g/l. This stock-solution was used for the following crystallization examples using 2,2'-(ethylenedioxy)diethyl amine (EDEA):

Example 7a

1 Equivalent EDEA; Ratio Methanol/Ethyl Acetate=1.5/10

Part of the pravastatin stock-solution obtained above (10 ml, 0.9 mmol pravastatin) was diluted with methanol (1 ml). Under stirring EDEA (70 µl, 0.47 mmol) in methanol (0.5 ml) was added drop-wise to this solution. The solution remained clear, even after cooling overnight to 0-5° C. After cooling to −20° C. overnight yellow oil precipitated. The oil was dissolved at room temperature and the solution was seeded with pravastatin 2,2'-(ethylenedioxy)diethyl amine crystals as obtained in Example 1. Seed did not dissolve and initiated crystallization. After stirring at room temperature overnight the crystals were filtered off, washed with a mixture of ethyl acetate (5 ml) and methanol (0.75 ml) and dried under vacuum at 30° C., yielding 0.25 g white powder with the same $^1$H NMR characteristics as described in Example 1.

Example 7b

1 Equivalent EDEA; Ratio Methanol/Ethyl Acetate=1/10; Reverse Addition

Under stirring part of the pravastatin stock-solution obtained above (10 ml, 0.9 mmol pravastatin) was added drop-wise to a solution of EDEA (70 µl, 0.47 mmol) in methanol (1 ml) at room temperature. After addition of 7 ml the solution became slightly turbid, due to the formation of small oil drops. One more ml was added, resulting in precipitation of oil. The mixture was seeded with pravastatin 2,2'-(ethylenedioxy)diethyl amine crystals as obtained in Example 1. As result the oil solidified. The remaining 2 ml of pravastatin solution was added and the mixture was divided into two equal portions. Portion 7b-1 was stirred overnight at room temperature, and portion 7b-2 was stored overnight at 0-5° C. Precipitate of portion 7b-1 was filtered off, washed with a mixture of ethyl acetate (5 ml) and methanol (0.5 ml) at room temperature, and dried under vacuum at 30° C., yielding 0.16 g of off-white powder.

Precipitate of portion 7b-2 was filtered off, washed with a mixture of ethyl acetate (5 ml) and methanol (0.5 ml) at 0-5° C., and dried under vacuum at 30° C., yielding 0.11 g of a sticky yellowish solid.

Example 7c

1.5 Equivalents EDEA; Ratio Methanol/Ethyl Acetate=1.5/10

Part of the pravastatin stock-solution obtained above (10 ml, 0.9 mmol pravastatin) was diluted with methanol (1.25 ml). Under stirring EDEA (105 μl, 0.7 mmol) in methanol (0.25 ml) was added drop-wise to this solution. The clear solution was seeded with pravastatin 2,2'-(ethylenedioxy)diethyl amine crystals as obtained in Example 1. Seed did not dissolve and initiated crystallization. After stirring at room temperature overnight the crystals were filtered off, washed with a mixture of ethyl acetate (5 ml) and methanol (0.75 ml) and dried under vacuum at 30° C., yielding 0.31 g white powder with the same $^1$H NMR characteristics as described in Example 1.

Example 7d

2 Equivalents EDEA; Ratio Methanol/Ethyl Acetate=1.5/10

Part of the pravastatin stock-solution obtained above (10 ml, 0.9 mmol pravastatin) was diluted with methanol (1.25 ml). Under stirring EDEA (140 μl, 0.94 mmol) in methanol (0.25 ml) was added drop-wise to this solution. The solution became slightly turbid. By gently heating a clear solution was obtained and seed of pravastatin 2,2'-(ethylenedioxy)diethyl amine crystals as obtained in Example 1 was added. After stirring at room temperature overnight the crystals were filtered off, washed with a mixture of ethyl acetate (5 ml) and methanol (0.75 ml) and dried under vacuum at 30° C., yielding 0.18 g white powder with the same $^1$H NMR characteristics as described in Example 1.

Example 7e

1.5 Equivalents EDEA; Ratio Methanol/Ethyl Acetate=1.5/10

Part of the pravastatin stock-solution obtained above (10 ml, 0.9 mmol pravastatin) was diluted with methanol (2 ml). Under stirring EDEA (70 μl, 0.47 mmol) in methanol (1 ml) was added drop-wise to this solution. This solution was diluted with ethyl acetate (10 ml) and EDEA (35 μl). The clear solution was seeded with pravastatin 2,2'-(ethylenedioxy)diethyl amine crystals as obtained in Example 1. After stirring at room temperature overnight the crystals were filtered off, washed with a mixture of ethyl acetate (5 ml) and methanol (0.75 ml) and dried under vacuum at 30° C., yielding 0.29 g off-white powder with the same $^1$H NMR characteristics as described in Example 1.

Example 7f

1.5 Equivalents EDEA; Ratio Methanol/Ethyl Acetate=1.5/10

Part of the pravastatin stock-solution obtained above (26 ml, 2.3 mmol pravastatin) was diluted with methanol (3.5 ml). At 35° C. EDEA (275 μl, 1.8 mmol) in methanol (0.5 ml) was added drop-wise under stirring to this solution. The clear solution was seeded with pravastatin 2,2'-(ethylenedioxy)diethyl amine crystals as obtained in Example 1. Seed did not dissolve and initiated crystallization at 33° C. After stirring at room temperature overnight the mixture was divided into two portions:

Portion 7f-1 (20 ml): crystals were filtered off, washed with a mixture of ethyl acetate (5 ml) and methanol (0.75 ml) and dried under vacuum at 30° C., yielding 0.58 g white powder with the same $^1$H NMR characteristics as described in Example 1.

Portion 7f-2 (10 ml); this portion was cooled to 5° C. for 4 hours. Next, crystals were filtered off, washed with a mixture of ethyl acetate (5 ml) and methanol (0.75 ml) and dried under vacuum at 30° C., yielding 0.30 g white powder with the same $^1$H NMR characteristics as described in Example 1.

The invention claimed is:

1. A salt of a carboxylic acid with a diamine of general structure [1]:

$$H_2N-(CH_2)_a-O-(CH_2)_b-(O)_c-(CH_2)_d-NH_2 \qquad [1]$$

wherein a is 1, 2, 3 or 4, b is 0, 1, 2, 3 or 4, c is 0 or 1, d is 1, 2, 3 or 4 and c is 0 when b is 0, and wherein the carboxylic acid is a fermentation product selected from the group consisting of arachidonic acid, biotin, cholic acid, compactin, docosahexaenoic acid, eicosapentaenoic acid, enteromycin, fusidic acid, helvolic acid, jasmonic acid, lactobacillic acid, laidlomycin, linoleic acid, linolenic acid, lovastatin, mevastatin, mycophenolic acid, penicillin G, penicillin V, pimaric acid, pravastatin, prostaglandin, retinoic acid, rifamycin B, shikimic acid and simvastatin.

2. A salt according to claim 1 wherein said diamine is selected from the group consisting of 2,2'-(ethylenedioxy)diethyl amine, 3,3'-(ethylenedioxy)dipropyl amine and 2,2'-oxybis(ethylamine).

3. A salt of a carboxylic acid with a diamine which is a pravastatin salt of 2,2'-(ethylenedioxy)diethyl amine or a mycophenolic acid salt of 2,2'-(ethylenedioxy)diethyl amine.

4. A salt according to claim 3 which is the bis-pravastatin salt of 2,2'-(ethylenedioxy)diethyl amine or the mono-mycophenolic acid salt of 2,2'-(ethylenedioxy)diethyl amine.

* * * * *